United States Patent
Sirinyan et al.

(10) Patent No.: US 7,384,938 B2
(45) Date of Patent: Jun. 10, 2008

(54) AQUEOUS FORMULATIONS OF PARASITICIDES FOR SKIN APPLICATIONS

(75) Inventors: Kirkor Sirinyan, Bergisch Gladbach (DE); Hubert Dorn, Wuppertal (DE); Ulrich Heukamp, Kurten (DE)

(73) Assignee: Bayer Aktiengesellschaft (DE)

( * ) Notice: Subject to any disclaimer, the term of this patent is extended or adjusted under 35 U.S.C. 154(b) by 402 days.

(21) Appl. No.: 10/347,003

(22) Filed: Jan. 17, 2003

(65) Prior Publication Data

US 2003/0162773 A1 Aug. 28, 2003

Related U.S. Application Data

(63) Continuation of application No. 09/622,660, filed as application No. PCT/EP99/00875 on Feb. 10, 1999, now abandoned.

(30) Foreign Application Priority Data

Feb. 23, 1998 (DE) ................. 198 07 633

(51) Int. Cl.
*A01N 43/40* (2006.01)
*A61K 31/54* (2006.01)
*A61K 31/535* (2006.01)

(52) U.S. Cl. .................... 514/226.8; 514/340
(58) Field of Classification Search ............. 514/226.8, 514/340, 226.08

See application file for complete search history.

*Primary Examiner*—San-Ming Hui
(74) *Attorney, Agent, or Firm*—Jessica Monachello

(57) ABSTRACT

The present invention relates to water-containing formulations for the dermal control of parasitic insects on animals, having the following composition
   a) agonists or antagonists of the nicotinic acetylcholine receptors of insects in a concentration of from 1 to 20% by weight based on the overall weight of the formulation;
   b) water in a concentration of from 2.5 to 15% by weight;
   c) solvents from the group alcohols such as benzyl alcohol, tetrahydrofuryl alcohol or optionally substituted pyrrolidones in a concentration of at least 20% by weight based on the overall weight of the formulation;
   d) solvents from the group of the cyclic carbonates or lactones in a concentration of from 5 to up to 50% by weight based on the overall weight of the formulation;
   e) if desired, further auxiliaries from the group thickeners, spreading agents, colorants, antioxidants, propellants, preservatives, adhesives, emulsifiers, in a concentration of from 0.025 up to 10% by weight based on the overall weight of the formulation.

6 Claims, No Drawings

AQUEOUS FORMULATIONS OF PARASITICIDES FOR SKIN APPLICATIONS

The present invention relates to water-containing formulations for the dermal control of parasitic insects on animals by means of agonists or antagonists of the nicotinergic acetylcholine receptors of insects.

Agonists or antagonists of the nicotinergic acetylcholine receptors of insects are known. They include the nicotinyl insecticides and especially the chloronicotinyl insecticides. Their use against fleas is known, for example, from WO 93/24002 and EP-A 682 869.

This invention, accordingly, provides novel water-containing formulations for dermal application of agonists or antagonists of the nicotinergic acetylcholine receptors of insects which are suitable in particular for the dermal control of parasitic insects such as fleas, lice or flies on animals and which are distinguished by their excellent storage stability at low temperature (down to −30° C.).

The formulations according to the invention have the following composition:
a) agonists or antagonists of the nicotinergic acetylcholine receptors of insects in a concentration of from 1 to 20% by weight based on the overall weight of the formulation;
b) water in a concentration of from 2.5 to 15% by weight based on the overall weight of the formulation;
c) solvents from the group alcohols such as benzyl alcohol, tetrahydrofuryl alcohol or optionally substituted pyrrolidones in a concentration of at least 20% by weight based on the overall weight of the formulation;
d) solvents from the group of the cyclic carbonates or lactones in a concentration of from 5 to 50% by weight based on the overall weight of the formulation;
e) if desired, further auxiliaries from the group thickeners, spreading agents, colorants, antioxidants, propellants, preservatives, adhesives, emulsifiers, preferably in a concentration of from 0.025 up to 10% by weight based on the overall weight of the formulation.

Agonists or antagonists of the nicotinergic acetylcholine receptors of insects are known, for example, from the European Published Specifications Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; the German Published Specifications Nos. 3 639 877, 3 712 307; the Japanese Published Specifications Nos. 03 220 176, 02 207 083, 63 307 857, 63 287 764, 03 246 283, 04 9371, 03 279 359, 03 255 072; the U.S. Pat. Nos. 5,034,524, 4,948,798, 4,918,086, 5,039,686, 5,034,404; the PCT Applications Nos. WO 91/17 659, 91/4965; the French Application No. 2 611 114; the Brazilian Application No. 88 03 621.

The compounds described in these publications and their preparation are expressly incorporated herein by way of reference.

These compounds can preferably be represented by the general formula (I)

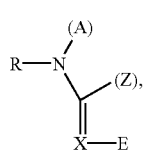

in which
R represents hydrogen, optionally substituted radicals from the group consisting of acyl, alkyl, aryl, aralkyl, heteroaryl or heteroarylalkyl;
A represents a monofunctional group from the series hydrogen, acyl, alkyl, aryl, or represents a bifunctional group which is linked to the radical Z;
E represents an electron-withdrawing radical;
X represents the radicals —CH═ or ═N—, it being possible for the radical —CH═ instead of an H atom to be linked to the radical Z;
Z represents a monofunctional group from the series alkyl, —O—R, —S—R,

where R represents identical or different radicals and is as defined above,
or represents a bifunctional group which is linked to the radical A or the radical X.

Particularly preferred compounds of the formula (I) are those in which the radicals are as defined below:
R represents hydrogen and also represents optionally substituted radicals from the series acyl, alkyl, aryl, aralkyl, heteroaryl, heteroarylalkyl, heterocyclyl-alkyl.
As acyl radicals there may be mentioned formyl, alkylcarbonyl, arylcarbonyl, alkylsulphonyl, arylsulphonyl, (alkyl)-(aryl)-phosphoryl, each of which may in turn be substituted.
As alkyl there may be mentioned $C_{1-10}$-alkyl, especially $C_{1-4}$-alkyl, specifically methyl, ethyl, i-propyl, sec- or t-butyl, each of which may in turn be substituted.
As aryl there may be mentioned phenyl, naphthyl, especially phenyl.
As aralkyl there may be mentioned phenylmethyl, phenylethyl.
As heteroaryl there may be mentioned heteroaryl having up to 10 ring atoms and N, O, S especially N as heteroatoms. Specifically there may be mentioned thienyl, furyl, thiazolyl, imidazolyl, pyridyl, benzothiazolyl.
As heteroarylalkyl there may be mentioned heteroarylmethyl, heteroarylethyl, heteroaryl preferably containing up to 6 ring atoms and N, O, S, especially N as heteroatoms, particularly preferably there may be mentioned the above-mentioned heteroaryl radicals.
As heterocyclyl there may be mentioned tetrahydrofuranyl.
As substituents there may be listed by way of example and preference:
alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being preferably fluorine, chlorine or bromine, especially fluorine, such as trifluoromethyl; hydroxyl; halogen, preferably fluorine, chlorine, bromine and iodine, especially fluorine, chlorine and bromine; cyano; nitro; amino; monoalkyl- and dialkylamino having preferably 1 to 4, in particular 1 or 2 carbon atoms per alkyl group, such as methylamino, methyl-ethyl-amino, n- and i-propylamino and methyl-n-butylamino; carboxyl; carbalkoxy having preferably 2 to 4, in particular 2 or 3 carbon atoms, such as carbomethoxy and carboethoxy; sulpho (—$SO_3H$); alkylsulphonyl having preferably 1 to 4, in particular 1 or 2 carbon atoms, such as methylsulphonyl and ethylsulphonyl; arylsulphonyl having preferably 6 or 10 aryl carbon atoms, such as phenylsulphonyl, and also heteroarylamino and heteroarylalkylamino such as chloropyridylamino and chloropyridylmethylamino.

A particularly preferably represents hydrogen and also represents optionally substituted radicals from the series acyl, alkyl, aryl, which are preferably as defined under R. A furthermore represents a bifunctional group. There may be mentioned optionally substituted alkylene having 1-4, in particular 1-2 carbon atoms, substituents which may be mentioned being the substituents listed earlier above, and it being possible for the alkylene groups to be interrupted by heteroatoms from the series N, O, S.

A and Z may, together with the atoms to which they are attached, form a saturated or unsaturated heterocyclic ring. The heterocyclic ring can contain a further 1 or 2 identical or different heteroatoms and/or hetero groups. Heteroatoms are preferably oxygen, sulphur or nitrogen, and hetero groups are preferably N-alkyl, where the alkyl in the N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, hexahydro-1,3,5-triazine, morpholine, oxadiazine, each of which may optionally be substituted preferably by methyl.

E represents an electron-withdrawing radical, in which context particular mention may be made of $NO_2$, CN, halogenoalkylcarbonyl such as 1-5-halogeno-$C_{1-4}$-carbonyl especially $COCF_3$, and also alkylsulphonyl and halogenoalkylsulphonyl, such as 1-5-halogeno-$C_1$-$C_4$-sulphonyl, in particular $SO_2CF_3$.

X represents —CH= or —N=

Z represents optionally substituted radicals alkyl, —OR, —SR, —NRR (R being identical or different), where R and the substituents are preferably each as defined above.

Z can form, apart from the abovementioned ring, together with the atom to which it is attached and with the radical

instead of X, a saturated or unsaturated heterocyclic ring. The heterocyclic ring can contain a further 1 or 2 identical or different heteroatoms and/or hetero groups. The heteroatoms are preferably oxygen, sulphur or nitrogen, and the hetero groups N-alkyl, in which case the alkyl or N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, morpholine and N-methyl-piperazine.

Particular mention may furthermore be made of the use of compounds of the formula (I) which are characterized in that the radicals in the formula (I) are as defined below:

R represents optionally substituted radicals from the series heteroarylmethyl or heteroarylethyl, heteroaryl which may be mentioned being: thienyl, furyl, thiazolyl, imidazolyl, pyridyl, benzothiazolyl.

As substituents there may be listed:
methyl, ethyl, methoxy, ethoxy, methylthio, ethylthio, trifluoromethyl; hydroxyl; fluorine, chlorine and bromine; cyano; nitro; amino;

A represents hydrogen and also represents a bifunctional, optionally substituted alkylene group having 2 carbon atoms which is linked to the radical Z, substituents which may be mentioned being the substituents listed earlier above, and it being possible for the alkylene group to be interrupted by 1 heteroatom from the series N, O, S, A and Z may, together with the atoms to which they are attached, form a saturated or unsaturated 5- or 6-membered heterocyclic ring. The heterocyclic ring can contain a further 1 or 2 identical or different heteroatoms and/or hetero groups. Heteroatoms are oxygen, sulphur or nitrogen and hetero groups are N-alkyl, where the alkyl in the N-alkyl group contains 1 or 2 carbon atoms.

E represents $NO_2$, CN,

X represents —CH= or —N=

Z represents optionally substituted radicals alkyl, —OR', —SR', —NR'R' (the radicals R' are identical or different), where R' and the substituents are each as defined below:

R' represents hydrogen and also represents optionally substituted radicals from the series acyl, alkyl, aryl, aralkyl, heteroaryl, heteroarylalkyl.

As acyl radicals there may be mentioned formyl, alkylcarbonyl, arylcarbonyl, alkylsulphonyl, arylsulphonyl, (alkyl)-(aryl)-phosphoryl.

As alkyl there may be mentioned $C_{1-4}$-alkyl.

As aryl there may be mentioned phenyl.

As aralkyl there may be mentioned phenylmethyl, phenylethyl.

As heteroarylalkyl there may be mentioned heteroarylmethyl, heteroarylethyl, where thienyl, furyl, thiazolyl, imidazolyl, pyridyl, and benzothiazolyl may be mentioned as heteroaryl.

As substituents of the radicals R' there may be listed:
methyl, ethyl, methoxy, ethoxy, methylthio, ethylthio, halogenoalkyl having 1 or 2 carbon atoms and 1 to 5 halogen atoms, the halogen atoms being identical or different and being fluorine, chlorine or bromine, hydroxyl; fluorine, chlorine and bromine; cyano; nitro; amino; monoalkyl- and dialkyl-amino preferably having 1 or 2 carbon atoms per alkyl group, carboxyl; carbalkoxy having 2 or 3 carbon atoms, sulpho (—$SO_3H$); alkylsulphonyl having 1 or 2 carbon atoms, phenylsulphonyl, chloropyridylamino and chloropyridylmethylamino.

As compounds which may be used with very particular preference in accordance with the invention, mention may be made of compounds of the general formulae (II), (III) and (IV):

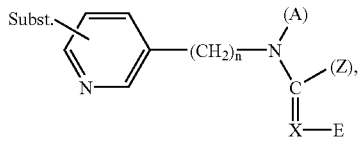
(II)
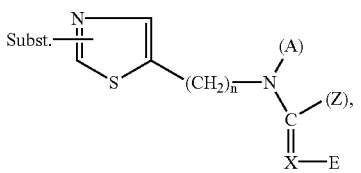
(III)
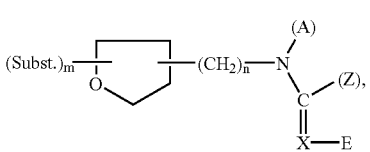
(IV)
in which
n represents 1 or 2,
m represents 0, 1 or 2,
Subst. represents one of the abovementioned substituents, in particular halogen, very particularly chlorine,
A, Z, X and E are each as defined above.
Specifically, the following compounds may be mentioned:
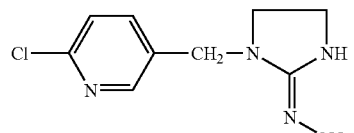
imidacloprid
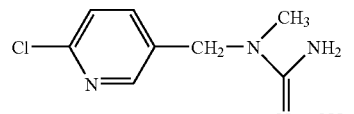
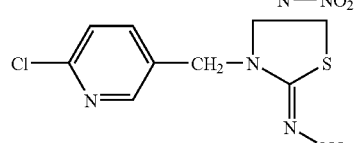
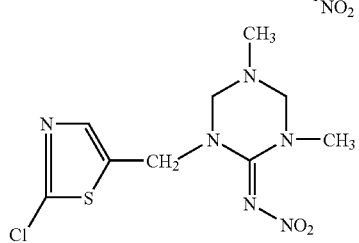
AKD 1022
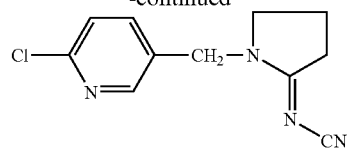
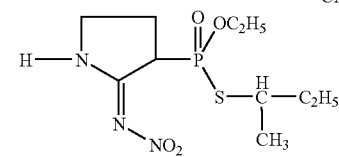
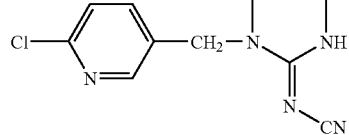
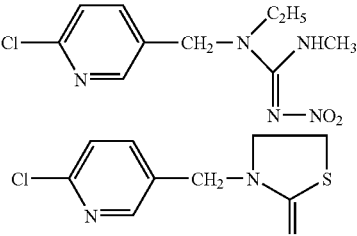
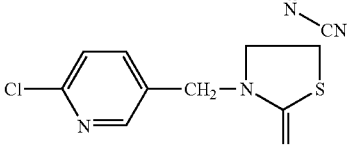
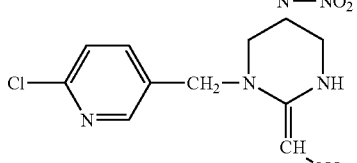
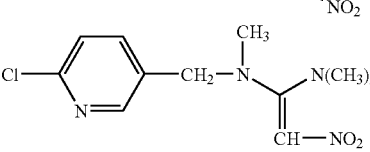
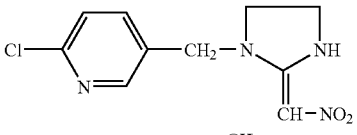
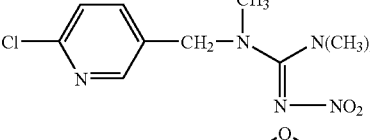
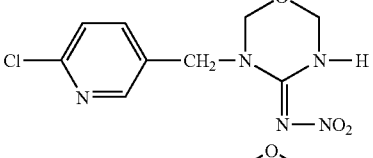
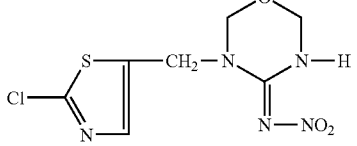

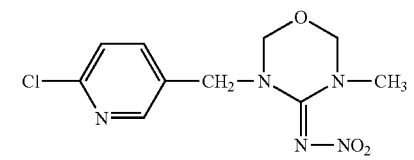
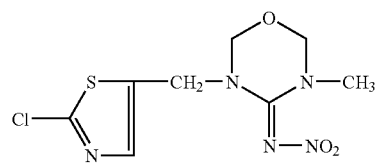
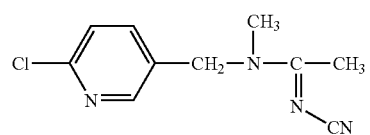
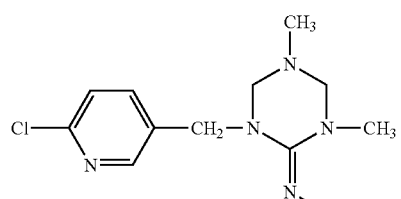
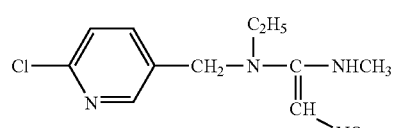
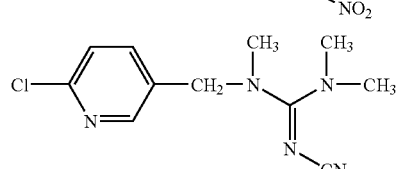
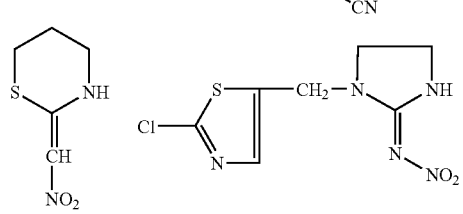
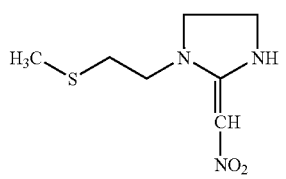
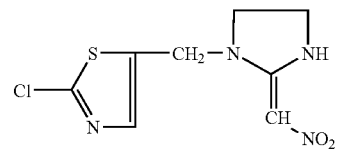
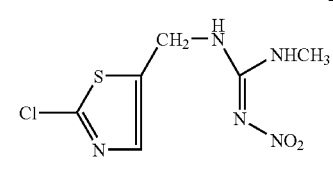
Ti435
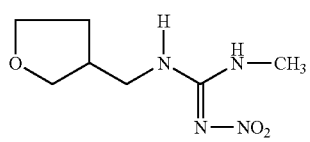
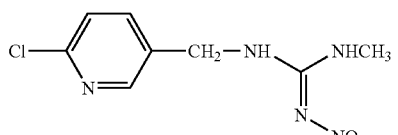
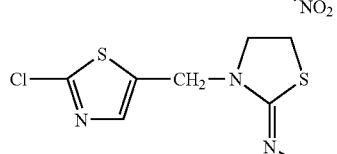
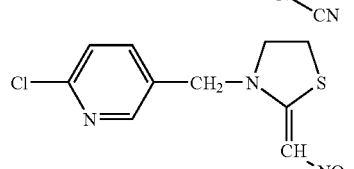
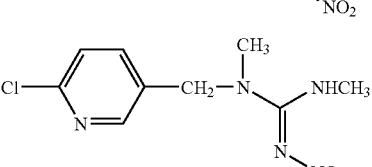
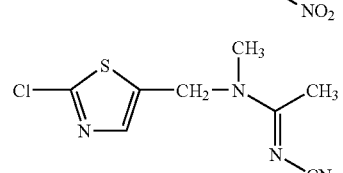
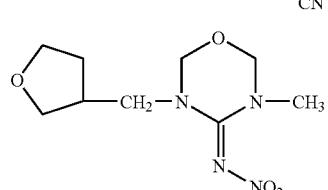
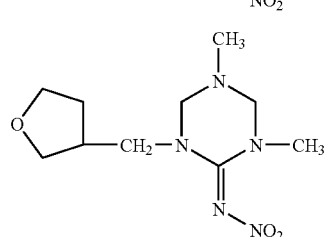
The following compounds may be particularly emphasized
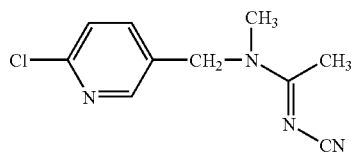

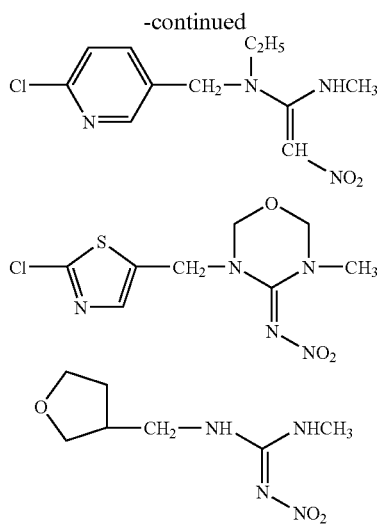

The following compounds may also be particularly emphasized

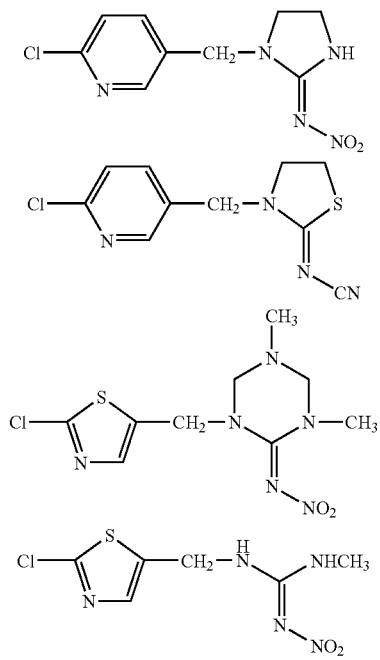

The formulations according to the invention contain the active substance in concentrations of from 0.1 to 20% by weight, preferably from 1 to 12.5% by weight.

In general it has proved to be advantageous to administer quantities of from about 0.5 to about 50 mg, preferably from 1 to 20 mg, of active compound per body weight per day in order to achieve effective results.

The formulation contains from 2.5 to 15% by weight of water, preferably from 4 to 8% by weight, particularly preferably about 5% by weight. The addition of water surprisingly results in a considerable improvement in the low-temperature stability of the formulation against precipitation of the active compound at low temperatures.

Suitable solvents are:

alcohols such as benzyl alcohol or tetrahydrofurfuryl alcohol or optionally substituted pyrrolidones such as 2-pyrrolidone, 1-($C_{2-20}$-alkyl)-2-pyrrolidone, in particular 1-ethylpyrrolidone, 1-octylpyrrolidone, 1-dodecylpyrrolidone, 1-isopropylpyrro-lidone, 1-(s- or t- or n-butyl)-pyrrolidone, 1-hexylpyrrolidone, 1-($C_{2-10}$-alkenyl)-2-pyrrolidone such as 1-vinyl-2-pyrrolidone, 1-($C_3$-g-cycloalkyl)-2-pyrrolidone such as 1-cyclohexylpyrrolidone, 1-($C_{1-6}$-hydroxyalkyl)-2-pyrrolidone, 1-($C_{1-6}$-alkoxy-$C_{1-6}$-alkyl)-2-pyrrolidone such as 1-(2-hydroxyethyl)-pyrrolidone, 1-(3-hydroxy-propyl)-pyrrolidone, 1-(2-methoxyethyl)-pyrrolidone, 1-(3-methoxypropyl)-pyrrolidone, and also 1-benzylpyrrolidone. Particular mention may be made of benzyl alcohol. These solvents are employed in a mixture with additional solvents (cosolvents).

They are present in a concentration of at least 40% by weight, preferably from 40 to 85% by weight, particularly preferably from 50 to 80% by weight.

Suitable cosolvents are: cyclic carbonates or lactones. As such there may be mentioned: ethylene carbonate, propylene carbonate, γ-butyrolactone.

They are present in a concentration from 5.0 up to 50% by weight, preferably from 7.5 to 50% by weight, particularly preferably from 10 to 50% by weight.

The sum of active compounds, solvents and auxiliaries must be 100% by weight.

Suitable further auxiliaries are: preservatives such as benzyl alcohol (not required if already present as solvent), p-hydroxybenzoic esters, n-butanol.

Thickeners such as: inorganic thickeners such as bentonites, colloidal silicic acid, aluminium monostearate, organic thickeners such as cellulose derivatives, polyvinyl alcohols, polyvinylpyrrolidones and copolymers thereof, acrylates and methacrylates.

Colorants which may be mentioned are all colorants where use on the animal is permitted, which may be dissolved or suspended.

Auxiliaries are also spreading oils such as di-2-ethylhexyl adipate, isopropyl myristate, dipropylene glycol pelargonate, cyclic and acyclic silicone oils such as dimeticones and also co- and terpolymers thereof with ethylene oxide, propylene oxide and formalin, fatty acid esters, triglycerides, fatty alcohols.

Antioxidants are sulphites or metabisulphites such as potassium metabisulphite, ascorbic acid, butylated hydroxytoluene, butylated hydroxyanisole, tocopherol and vitamin E.

Their amount may be varied widely in the range from 0.01 to 5.0% (based on the total formulation), and preference is given to amounts between 0.05 to 3.0%. The particularly preferred amounts are in the range from 0.075 to 2.5%. Preferred antioxidants are butylated hydroxytoluene, tocopherol and vitamin E.

Light stabilizers are, for example, substances from the class of the benzophenones or novantisol acid.

Adhesives are, for example, cellulose derivatives, starch derivatives, polyacrylates, naturally occurring polymers such as alginates, gelatin.

Auxiliaries are also emulsifiers such as nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as di-Na N-lauryl-β-iminodipropionate or lecithin;

anionic surfactants, such as Na-lauryl sulphate, fatty alcohol ether sulphates, mono/dialkyl polyglycol ether orthophosphoric ester monoethanolarnine salt;

cationic surfactants such as cetyltrimethylammonium chloride.

Further auxiliaries are compositions with which the formulations according to the invention can be sprayed or squirted onto the skin. These are the conventional propellant gases required for spray cans, such as propane, butane, dimethyl ether, $CO_2$ or halogenated lower alkanes, or mixtures thereof with one another.

While being of low mammalian toxicity the formulations according to the invention are suitable for the control of parasitic insects which are encountered in animal keeping and animal breeding in domestic and productive animals and in zoo and laboratory animals and animals used for experimentation and in the pursuit of hobbies. In this context they are active against all or individual stages of development of the pests and against resistant and normally sensitive species of the pests.

The pests include:
from the order of the Anoplura e.g. Haematopinus spp., Linognathus spp., Solenopotes spp., Pediculus spp., Pthirus spp.;
from the order of the Mallophaga e.g. Trimenopon spp., Menopon spp., Eomenacanthus spp., Menacanthus spp., Trichodectes spp., Felicola spp., Damalinea spp., Bovicola spp;
from the order of the Diptera e.g. Chrysops spp., Tabanus spp., Musca spp., Hydrotaca spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.
From the order of the Siphonaptera e.g. Ctenocephalides spp., Echidnophaga spp., Ceratophyllus spp.

Particular mention may be made of the action against Siphonaptera, especially against fleas.

The productive and breeding animals include mammals such as, for example, cattle, horses, sheep, pigs, goats, camels, water buffalo, donkeys, rabbits, fallow deer, reindeer, fur-bearing animals such as, for example, mink, chinchilla or racoon, birds such as, for example, chickens, geese, turkeys, ducks.

Laboratory animals and those for experimentation include mice, rats, guinea pigs, golden hamsters, dogs and cats.

The animals used in the pursuit of hobbies include dogs and cats.

Administration can be effected both prophylactically and therapeutically.

In the formulations according to the invention, it is also possible for further active compounds to be present. The further active compounds include insecticides such as phosphorus-containing compounds, i.e. phosphates or phosphonates, natural or synthetic pyrethroids, carbamates, amidines, juvenile hormones and juvenoid synthetic active compounds, and chitin synthesis inhibitors such as diaryl ethers and benzoylureas.

The phosphates or phosphonates include:
O-ethyl-O-(8-quinolyl)phenyl thiophosphate (quintiofos),
O,O-diethyl I-(3-chloro-4-methyl-7-coumarinyl)-thiophosphate (coumaphos),
O,O-diethyl O-phenylglycoxylonitrile oxime thiophosphate (phoxirn), O,O-diethyl O-cyanochlorobenzaldoxime thiophosphate (chlorphoxim),
O,O-diethyl O-(4-bromo-2,5-dichlorophenyl) phosphorothionate (bromophos-ethyl),
O,O,O',O'-tetraethyl S,S'-methylene-di(phosphorodithionate) (ethion),
2,3-p-dioxanedithiol S,S-bis(O,O-diethyl phosphorodithionate),
2-chloro-1-(2,4-dichlorophenyl)-vinyl diethyl phosphate (chlorfenvinphos),
O,O-dimethyl O-(3-methyl-4-methylthiophenyl) thionophosphate (fenthion).

The carbamates include:
2-isopropoxyphenyl methylcarbamate (propoxur),
1-naphthyl N-methylcarbamate (carbaryl).

The synthetic pyrethroids include
3-[2-(4-chlorophenyl)-2-chlorovinyl]-2,2-dimethyl-cyclopropanecarboxylic acid (α-cyano-4-fluoro-3-phenoxy)-benzyl ester (flumethrin),
α-cyano(4-fluoro-3-phenoxy)-benzyl 2,2-dimethyl-3-(2,2-dichlorovinyl)-cyclopro-panecarboxylate (cyfluthrin) and its enantiomers and stereomers,
α-cyano-3-phenoxybenzyl (±)-cis, trans-3-(2,2-dibromovinyl)-2,2-dimethylcyclopro-panecarboxylate (deltamethrin),
α-cyano-3-phenoxybenzyl 2,2-dimethyl-3-(2,2-dichlorovinyl)-cyclopropane-carboxylate (cypermethrin),
3-phenoxybenzyl (±)-cis, trans-3-(2,2-dichlorovinyl)-2,2-dimethylcyclopropane-carboxylate (permethrin),
α-cyano-3-phenoxy-benzyl α-(p-C1-phenyl)-isovalerate (fenvalerate),
2-cyano-3-phenoxybenzyl 2-(2-chloro-α,α,α-trifluoro-p-toluidino)-3-methylbutyrate (fluvalinate).

The amidines include:
3-methyl-2-[2,4-dimethyl-phenylimino]-thiazoline,
2-(4-chloro-2-methylphenylimino)-3-methylthiazolidine,
2-(4-chloro-2-methylphenylimino)-3-(isobutyl-1-enyl)-thiazolidine
1,5-bis-(2,4-dimethylphenyl)-3-methyl-1,3,5-triazapenta-1,4-diene (amitraz).

Cyclic macroliths such as invermectins and abamectins. In this context there may be mentioned, for example, 5-O-dimethyl-22,23-dihydroavermectin-$A_{1a}$, -22,23-dihydroavermectin $B_{1a}$ and 22,23-dihydroavermectin $B_{b1}$ (cf. for example WHO. F.A. Series 27, pp. 27-73 (1991)). The juvenile hormones and juvenile hormone-like substances include, in particular, compounds of the following formulae:

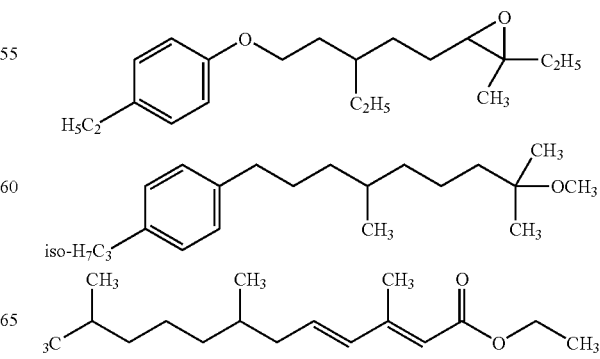

-continued

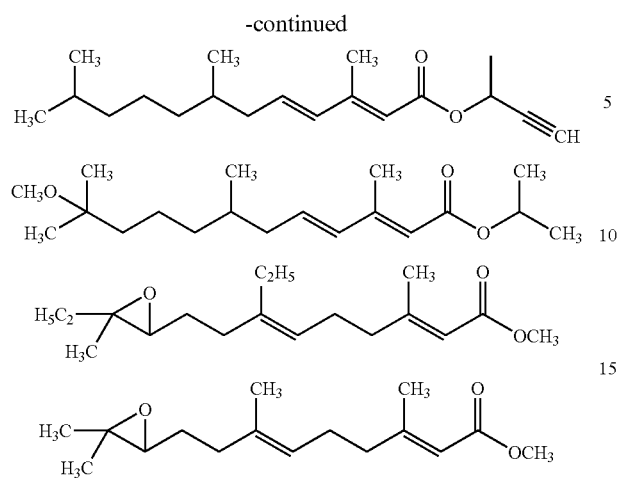

The substituted diaryl ethers include, in particular

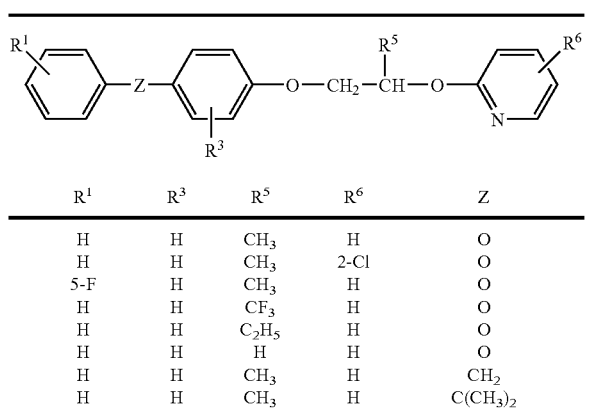

| R¹  | R³ | R⁵    | R⁶   | Z        |
|-----|----|-------|------|----------|
| H   | H  | CH₃   | H    | O        |
| H   | H  | CH₃   | 2-Cl | O        |
| 5-F | H  | CH₃   | H    | O        |
| H   | H  | CF₃   | H    | O        |
| H   | H  | C₂H₅  | H    | O        |
| H   | H  | H     | H    | O        |
| H   | H  | CH₃   | H    | CH₂      |
| H   | H  | CH₃   | H    | C(CH₃)₂  |

The benzoylureas include compounds of the formula

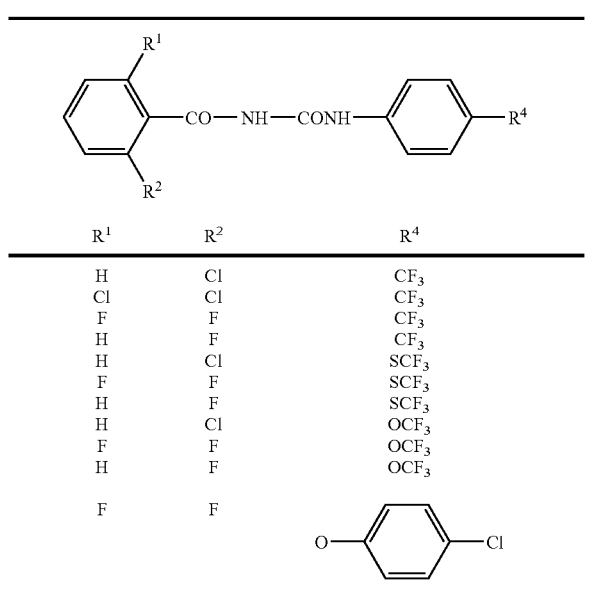

| R¹ | R² | R⁴ |
|----|----|-----|
| H  | Cl | CF₃ |
| Cl | Cl | CF₃ |
| F  | F  | CF₃ |
| H  | F  | CF₃ |
| H  | Cl | SCF₃ |
| F  | F  | SCF₃ |
| H  | F  | SCF₃ |
| H  | Cl | OCF₃ |
| F  | F  | OCF₃ |
| H  | F  | OCF₃ |
| F  | F  | —O—⟨C₆H₄⟩—Cl |

-continued

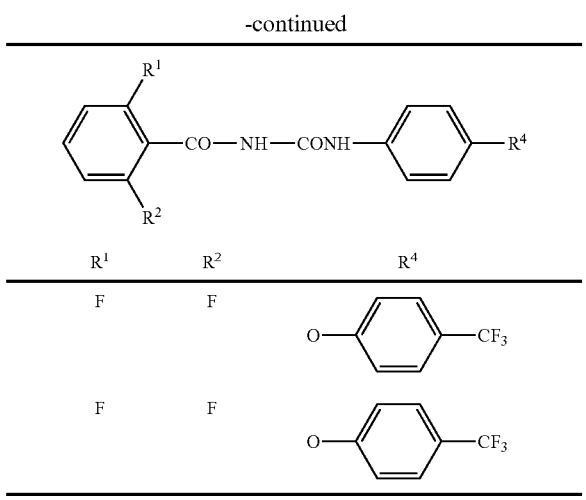

| R¹ | R² | R⁴ |
|----|----|-----|
| F  | F  | —O—⟨C₆H₄⟩—CF₃ |
| F  | F  | —O—⟨C₆H₄⟩—CF₃ |

The triazines include compounds of the formula

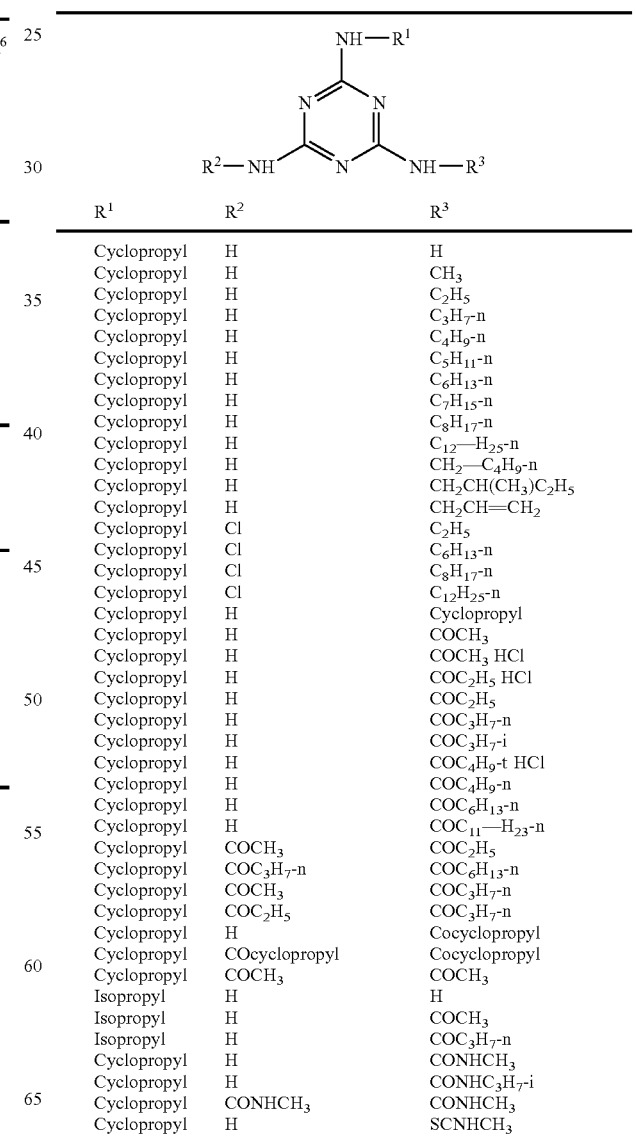

| R¹ | R² | R³ |
|----|----|-----|
| Cyclopropyl | H | H |
| Cyclopropyl | H | CH₃ |
| Cyclopropyl | H | C₂H₅ |
| Cyclopropyl | H | C₃H₇-n |
| Cyclopropyl | H | C₄H₉-n |
| Cyclopropyl | H | C₅H₁₁-n |
| Cyclopropyl | H | C₆H₁₃-n |
| Cyclopropyl | H | C₇H₁₅-n |
| Cyclopropyl | H | C₈H₁₇-n |
| Cyclopropyl | H | C₁₂—H₂₅-n |
| Cyclopropyl | H | CH₂—C₄H₉-n |
| Cyclopropyl | H | CH₂CH(CH₃)C₂H₅ |
| Cyclopropyl | H | CH₂CH=CH₂ |
| Cyclopropyl | Cl | C₂H₅ |
| Cyclopropyl | Cl | C₆H₁₃-n |
| Cyclopropyl | Cl | C₈H₁₇-n |
| Cyclopropyl | Cl | C₁₂H₂₅-n |
| Cyclopropyl | H | Cyclopropyl |
| Cyclopropyl | H | COCH₃ |
| Cyclopropyl | H | COCH₃ HCl |
| Cyclopropyl | H | COC₂H₅ HCl |
| Cyclopropyl | H | COC₂H₅ |
| Cyclopropyl | H | COC₃H₇-n |
| Cyclopropyl | H | COC₃H₇-i |
| Cyclopropyl | H | COC₄H₉-t HCl |
| Cyclopropyl | H | COC₄H₉-n |
| Cyclopropyl | H | COC₆H₁₃-n |
| Cyclopropyl | H | COC₁₁—H₂₃-n |
| Cyclopropyl | COCH₃ | COC₂H₅ |
| Cyclopropyl | COC₃H₇-n | COC₆H₁₃-n |
| Cyclopropyl | COCH₃ | COC₃H₇-n |
| Cyclopropyl | COC₂H₅ | COC₃H₇-n |
| Cyclopropyl | H | Cocyclopropyl |
| Cyclopropyl | COcyclopropyl | Cocyclopropyl |
| Cyclopropyl | COCH₃ | COCH₃ |
| Isopropyl | H | H |
| Isopropyl | H | COCH₃ |
| Isopropyl | H | COC₃H₇-n |
| Cyclopropyl | H | CONHCH₃ |
| Cyclopropyl | H | CONHC₃H₇-i |
| Cyclopropyl | CONHCH₃ | CONHCH₃ |
| Cyclopropyl | H | SCNHCH₃ |

-continued

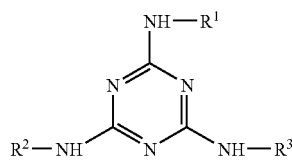

| R¹ | R² | R³ |
|---|---|---|
| Cyclopropyl | H | CONHCH₂CH=CH₂ |
| Cyclopropyl | CONHCH₂CH=CH₂ | CONHCH₂CH=CH₂ |
| Cyclopropyl | CSNHCH₃ | CSNHCH₃ |

Particular emphasis should be given to the further active compounds having the common names propoxur, cyfluthrin, flumethrin, pyriproxyfen, methoprene, diazinon, amitraz, fenthion, levamisol and ivermectin.

In the examples which follow, the active compound employed is 1-[(6-chloro-3-pyridinyl)methyl]-N-nitro-2-imidazolidinium (common name imidacloprid).

The formulations according to the invention are distinguished by their stability at temperatures in the range from +60° C. to −30° C. For this reason, no particular provisions have to be made for their storage and for their shipping.

EXAMPLE 1

| | |
|---|---|
| imidacloprid | 10 g |
| water | 10 g |
| propylene carbonate | 45 g |
| benzyl alcohol | 34.8 g |
| ® Belsil DMC 6031 | 1 g |
| (A polysiloxane copolymer from Wacker GmbH, D-81737 Munich) | |
| butylated hydroxytoluene | 0.2 g |

EXAMPLE 2

| | |
|---|---|
| imidacloprid | 10 g |
| water | 10 g |
| n-octyl-2-pyrrolidone | 34.5 g |
| γ-butyrolactone | 44.5 g |
| ® Belsil L 066 | 1 g |
| (A polysiloxane copolymer from Wacker GmbH, D-81737 Munich) | |

EXAMPLE 3

| | |
|---|---|
| imidacloprid | 10 g |
| water | 10 g |
| ethylene carbonate | 5 g |
| benzyl alcohol | 74.8 g |
| butylated hydroxytoluene | 0.1 g |
| ® Belsil DMC 6031 | 0.1 g |
| (polysiloxane copolymer) | |

EXAMPLE 4

| | |
|---|---|
| imidacloprid | 10.0 g |
| benzyl alcohol | 62.4 g |
| propylene carbonate | 17.5 g |
| water | 10.0 g |
| butylated hydroxytoluene | 0.1 g |

EXAMPLE 5

| | |
|---|---|
| imidacloprid | 10.0 g |
| benzyl alcohol | 65.0 g |
| propylene carbonate | 15.0 g |
| isopropyl myristate | 3.8 g |
| water | 6.0 g |
| butylated hydroxytoluene | 0.2 g |

EXAMPLE 6

| | |
|---|---|
| imidacloprid | 10.0 g |
| benzyl alcohol | 62.5 g |
| propylene carbonate | 17.4 g |
| butylated hydroxytoluene | 0.1 g |
| water | 10.0 g |

EXAMPLE 7

| | |
|---|---|
| imidacloprid | 10.0 g |
| benzyl alcohol | 70.0 g |
| propylene carbonate | 17.4 g |
| water | 2.5 g |
| butylated hydroxytoluene | 0.1 g |

EXAMPLE 8

| | |
|---|---|
| imidacloprid | 10.0 g |
| pyriproxyfen | 1.0 g |
| benzyl alcohol | 65.0 g |
| water | 5.0 g |
| propylene carbonate | 18.9 g |
| butylated hydroxytoluene | 0.1 g |

EXAMPLE 9

| | |
|---|---|
| imidacloprid | 10.0 g |
| triflumuron | 2.5 g |
| benzyl alcohol | 60.0 g |

| | |
|---|---|
| water | 7.5 g |
| propylene carbonate | 27.5 g |

EXAMPLE 10

| | |
|---|---|
| imidacloprid | 10.0 g |
| flumetrin | 2.0 g |
| benzyl alcohol | 60.0 g |
| propylene carbonate | 18.0 g |
| water | 10.0 g |

EXAMPLE 11

| | |
|---|---|
| imidacloprid | 10.0 g |
| benzyl alcohol | 60.0 g |
| ethylene carbonate | 10.0 g |
| propylene carbonate | 10.0 g |
| water | 9.8 g |
| butylated hydroxytoluene | 0.2 g |

EXAMPLE 12

| | |
|---|---|
| imidacloprid | 10.0 g |
| benzyl alcohol | 67.0 g |
| propylene carbonate | 17.4 g |
| vitamin E | 0.6 g |
| water | 5.0 g |

Use Example A 4 ml of the formulation described in Example 1 were poured onto the back of a dog weighing 40 kg which was infested with fleas. The following results were obtained:

| Period of time | Number of fleas per dog | | |
|---|---|---|---|
| Day | untreated | treated | % action |
| −1 infestation with 200 fleas | | | |
| 0 treatment and counting | 80 | 0 | 100 |
| 5, 8 infestation with 200 fleas | | | |
| 9 counting | 90 | 0 | 100 |
| 15 infestation with 200 fleas | | | |
| 16 counting | 110 | 0 | 100 |
| 19 infestation with 200 fleas (untreated animals) 250 fleas (treated animals) | | | |
| 20 counting | 75 | 0 | 100 |
| 26 infestation with 200 fleas | | | |
| 27 counting | 80 | 0 | 100 |

Use Example B 2 ml of the solution according to Example 4 were placed on the shoulders of a dog weighing 20 kg. The animal was infested with 200 fleas after 1 and after 6 days of treatment. On day 3 and on day 7, respectively, after treatment, the fleas remaining on the dog were counted. No living fleas were found. The action was 100%.

Use Example C 0.8 ml of the solution according to Example 4 was placed on the shoulders of a dog weighing ~8 kg. The animal was infected with 150 fleas after 3 and after 7 days of treatment. On day 3 and on day 7, respectively, after treatment, the fleas remaining on the dog were counted. No living fleas were found. The action was 100%.

Determination of the stability:

To determine the stability, the samples were stored for 4 weeks at temperatures of −30° C., −10° C., 0° C., +20° C., +30° C., +50° C. and +60° C., and their active compound concentration was then examined by HPLC, density, refractive index, external quality and colour. With the aid of these investigations, the stability of the formulations could be illustrated.

The invention claimed is:

1. A water-containing formulation for the dermal control of parasitic insects on animals by means of agonists or antagonists of the nicotinic acetylcholine receptors of insects, comprising:
   a) agonists or antagonists of the nicotinic acetylcholine receptors of insects in a concentration of from 1 to 20% by weight based on the overall weight of the formulation, wherein the agonists or antagonists are selected from one or more compounds of formula (I)

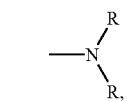

in which

R represents hydrogen or optionally substituted radicals selected from the group consisting of acyl, alkyl, aryl, aralkyl, heteroaryl and heteroarylalkyl;

A represents a monofunctional group selected from the group selected form the group consisting hydrogen, acyl, alkyl, and aryl, or represents a bifunctional group which is linked to the radical Z;

E represents an electron-withdrawing radical;

X represents the radical —CH═or═N, wherein the radical —CH═ instead of an H atom, may be linked to the radical Z;

Z represents a monofunctional group selected from the group consisting alkyl, O—R,—S—R, and

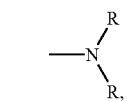

where the radicals R are identical or different and are each as defined above, or represents a bifunctional group which is linked to the radical A or the radical X;
b) water in a concentration of from 2.5 to 15% by weight based on the overall weight of the formulation;
c) solvents selected from the group consisting of alcohols and optionally substituted pyrrolidones, in a concentration of at least 20% by weight based on the overall weight of the formulation;
d) solvents selected from the group consisting of cyclic carbonates and lactones, in a concentration of from 5 to 50% by weight based on the overall weight of the formulation;
e) optionally, auxiliaries selected from the group consisting of thickeners, spreading agents, colorants, antioxidants, propellants, preservatives, adhesives, and emulsifiers.

2. The water-containing formulation of claim 1, wherein R represents hydrogen or optionally substituted radicals selected from the group consisting of acyl, alkyl, aryl, aralkyl, heteroaryl, heteroarylalkyl, and heterocyclylalkyl,
wherein
acyl radicals are selected from the group consisting of formyl, alkylcarbonyl, aryl-carbonyl, alkylsulphonyl, arylsulphonyl, (alkyl-)-(aryl-) phosphoryl, each of which is optionally substituted,
alkyl is $C_{1-10}$-alkyl, which is optionally substituted,
aryl is selected from the group consisting of phenyl, and naphthyl,
aralkyl is selected from the group consisting of phenylmeth and phenylethyl,
heteroary is selected from the group consisting of theinyl, furyl, thiazolyl, imidazolyl, pyridyl, and benzothizolyl,
heteroarylalkyl is selected from the group consisting of heteroarylmethyl and heteroarylethyl, wherein the heteroaryl radicals contain up to 6 ring atoms and heteroatoms selected from the group consisting of N, O, and S,
heterocyclyl is tetrahydrofuranyl,
and wherein substituents are selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms and wherein the halogen atoms may be identical or different and are selected from the group consisting of fluorine, choloring or bromine, hydroxyl, halogen, cyano, nitro, amino, monoalkyl and dialkylamino having 1 to 4 carbon atoms per alkyl group, carboxyl, carbalkoxy having 2 to 4 carbon atoms, sulpho (—$SO_3H$); alkylsulphonyl having 1 to 4 carbon atoms, phenylsulphonyl chioropyridylamin and chlorophridylethylamino;
A represents hydrogen or optionally substituted radicals selected from the group consisting of acyl, alkyl, aryl, which are defined above
or
A represents the bifunctional group optionally substituted alkylene having 1-4 carbon atoms, wherein the substituents are as defined above, and the alkylene groups may be interrupted by heteroatoms selected from the group consisting of N, O, and S,
or
A and Z may, together with the atoms to which they are attached, form a saturated or unsaturated heterocyclic ring wherein said heterocyclic ring is selected from the group consisting of pyrrolidine, piperidine, piperazine, hexamethyleneimine, hexahydro-1,3,5-triazine, morpholine, and oxadiazine, each of which may optionally be substituted by methyl,
E represents an electron-withdrawing radical;
X represents —CH= or —N=;
Z represents optionally substituted radicals alkyl, —OR, —SR, —NRR (wherein R may be identical or different);
and wherein R and the substituents are each as defined above,
or
Z can form together with the atom to which it is attached and with the radical

instead of X, a saturated or unsaturated heterocyclic ring wherein said heterocyclic ring is selected from the group consisting of pyrrolidine, piperidine, piperazine, hexamethyleneimine, morpholine and N-methylpiperazine.

3. The water-containing formulation of claim 1, wherein R represents optionally substituted radicals selected from the group consisting of heteroarylmethyl and heteroarylethyl, wherein the heteroaryl may be selected from the group consisting thienyl, furyl, thiazolyl, imidazolyl, pyridyl, and benzothiazolyl and the radical may be optionally substituted with methyl, ethyl, methoxy, ethoxy, methylthio, ethylthio, trifluoromethyl; hydroxyl; fluorine, chlorine, bromine, cyano, nitro, or amino;
A represents hydrogen or a bifunctional optionally substituted alkylene group having 2 carbon atoms which is linked to the radical Z, wherein the substituents are as described above, the alkylene group be interrupted by 1 heteroatom selected from the group consiting of N, O, and S,
or
A and Z may, together with the atoms to which they are attached, form a saturated or unsaturated 5- or 6-membered heterocyclic ring wherein the heterocyclic ring may contain a further 1 or 2 identical or different heteroatoms and/or hetero groups, and wherein the heteroatoms are oxygen, sulphur or nitrogen, and hetero groups are N-alkyl, where the alkyl in the N-alkyl group contains 1 or 2 carbon atoms;
E represents $NO_2$, CN;
X represents —CH= or —N=;
Z represents optionally substituted radicals alkyl, —OR', —SR', or —NR'R' (wherein the radicals R' are identical or different wherein)
R' represents hydrogen or optionally substituted radicals selected from the group consisting of acyl, alkyl, aryl, aralkyl, heteroaryl, and heteroarylalkyl,
wherein
acyl radicals are selected from the group consisting of formyl, alkylcarbonyl, arylcarbonyl, alkylsulphonyl, arylsulphonyl, and (alkyl-)-(aryl-)-phosphoryl,
alkyl is $C_{1-4}$-alkyl,
aryl is phenyl,
aralkyl is phenylmethyl, or phenylethyl,
heteroarylalkyl is heteroarylmethyl, or heteroarylethyl, and wherein the heteroaryl is selected from the group consisting of thienyl, furyl, thiazolyl, imidazolyl, pyridyl, and benzothiazolyl, and wherein substituents of the radicals R' are selected from the group consisting of methyl, ethyl, methoxy, ethoxy, methylthio, ethylthio, halogenoalkyl having 1 or 2 carbon atoms and 1 to 5 halogen atoms and wherein the halogen atoms are identical or different and are fluorine, chlorine or bromine, hydroxyl; fluorine, chlorine, bromine, cyano, nitro; amino; monoalkyl- and dialkylamino having 1 or 2 carbon atoms per alkyl group, carboxyl; carbalkoxy having 2 or 3 carbon atoms, sulpho (—SO$_3$H); alkylsulphonyl having 1 or 2 carbon atoms, phenylsulphonyl, chloropyridylamino and chloropyridylmethylamino.

4. The water-containing formulations of claim 1, wherein the agonists or antagonists are selected from one or more compounds of formula (II), (III) and (IV)

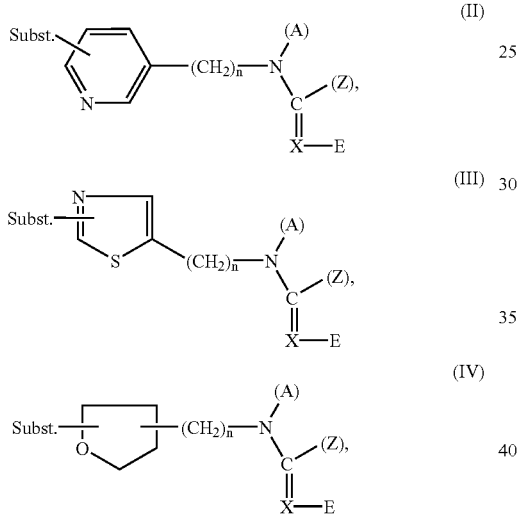

wherein n represents 1 or 2, m represents 0, 1 or 2,

Subst. represents one of the substituents as defined in claims 2 or 3,

A, Z, X and E are each as defined in claims 2 or 3.

5. The water-containing formulation of claim 1, wherein one or more of the compounds is selected from

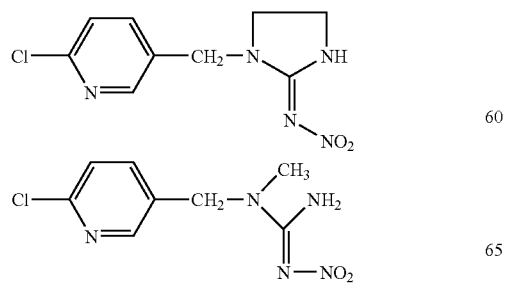

-continued

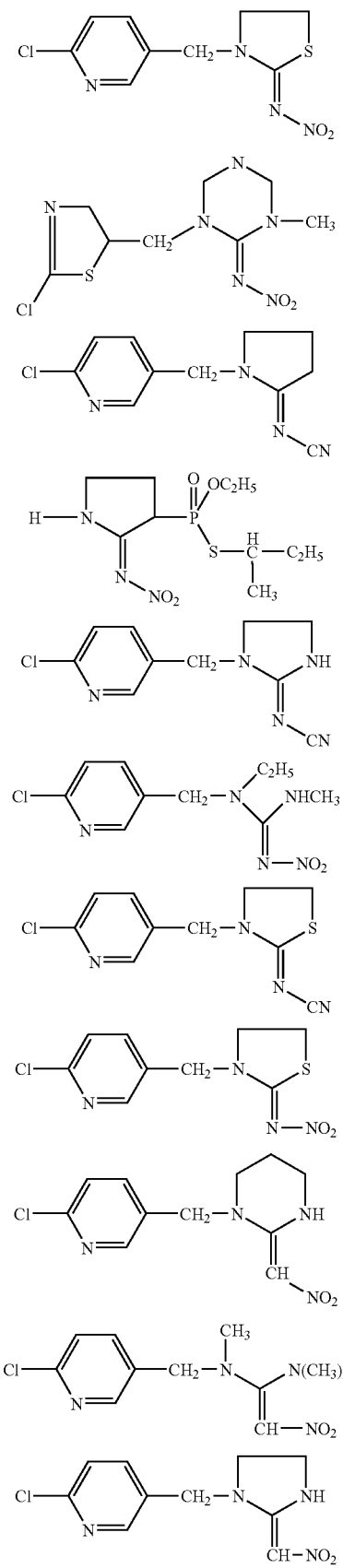

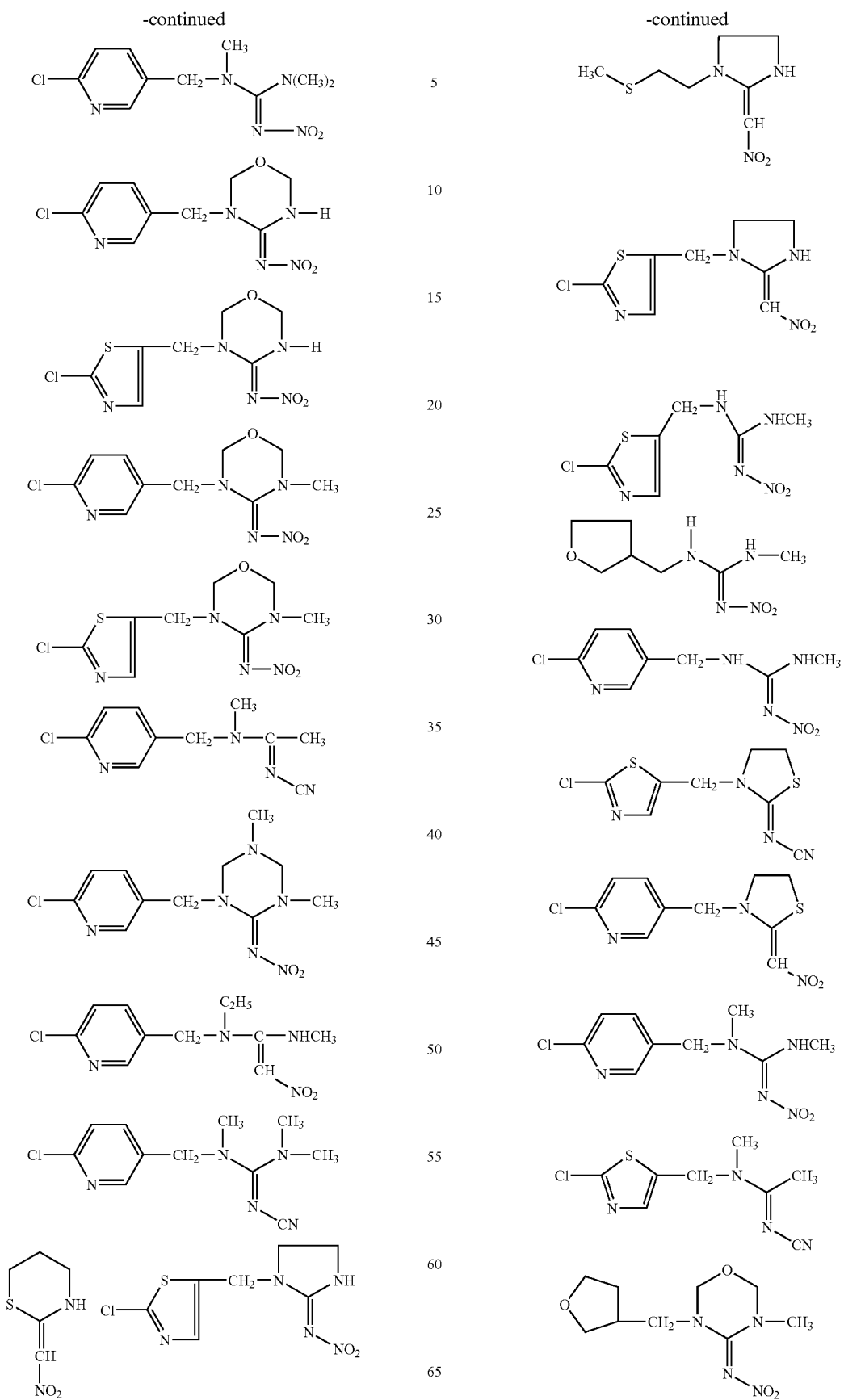

-continued
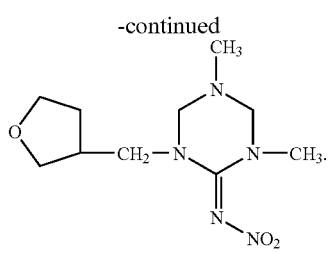
6. A process for preparing a water-containing formulation of claim 1, comprising mixing the compound(s) with water and solvent(s) to give a homogeneous solution and, optionally adding auxiliaries.
* * * * *